US00PP23017P2

(12) United States Plant Patent
Dümmen

(10) Patent No.: US PP23,017 P2
(45) Date of Patent: Sep. 4, 2012

(54) ***ARTEMISIA* PLANT NAMED 'DUEPARETHIO'**

(50) Latin Name: *Artemisia arborescens*
Varietal Denomination: Dueparethio

(75) Inventor: Tobias Dümmen, Rheinberg (DE)

(73) Assignee: Capital Green Investments Ltd., Grand Cayman (KY)

( * ) Notice: Subject to any disclaimer, the term of this patent is extended or adjusted under 35 U.S.C. 154(b) by 0 days.

(21) Appl. No.: 13/317,906

(22) Filed: Oct. 31, 2011

(51) Int. Cl.
*A01H 5/00* (2006.01)

(52) U.S. Cl. ..... Plt./373; Plt./263.1

(58) Field of Classification Search ..... Plt./373, Plt./263.1
See application file for complete search history.

*Primary Examiner* — June Hwu
*Assistant Examiner* — Louanne Krawczewicz Myers
(74) *Attorney, Agent, or Firm* — C. A. Whealy

(57) ABSTRACT

A new and distinct cultivar of *Artemisia* plant named 'Dueparethio' characterized by its relatively compact, upright and somewhat outwardly spreading growth habit; freely branching habit; moderately vigorous to vigorous growth habit; greyed green-colored leaves; and good garden performance.

1 Drawing Sheet

Botanical designation: *Artemisia arborescens*.
Cultivar denomination: 'DUEPARETHIO'.

BACKGROUND OF THE INVENTION

The present invention relates to a new and distinct cultivar of *Artemisia* plant, botanically known as *Artemisia arborescens* and hereinafter referred to by the name 'Dueparethio'.

The new *Artemisia* plant is a product of a planned breeding program conducted by the Inventor in Rheinberg, Germany. The objective of the breeding program is to create new compact *Artemisia* plants with greyed green-colored leaves.

The new *Artemisia* plant originated from a cross-pollination made by the Inventor in February, 2008 in Rheinberg, Germany of a proprietary selection of *Artemisia arborescens* identified as code number A07-0231-2, not patented, as the female, or seed, parent with a proprietary selection of *Artemisia arborescens* identified as code number A07-0109-4, not patented, as the male, or pollen, parent. The new *Artemisia* plant was discovered and selected by the Inventor as a single flowering plant from within the progeny of the stated cross-pollination in a controlled greenhouse environment in Rheinberg, Germany in May, 2010.

Asexual reproduction of the new *Artemisia* plant by terminal cuttings in a controlled greenhouse environment in Rheinberg, Germany since June, 2010 has shown that the unique features of this new *Artemisia* plant are stable and reproduced true to type in successive generations.

SUMMARY OF THE INVENTION

Plants of the new *Artemisia* have not been observed under all possible environmental conditions and cultural practices. The phenotype may vary somewhat with variations in environmental conditions such as temperature, daylight and light intensity without, however, any variance in genotype.

The following traits have been repeatedly observed and are determined to be the unique characteristics of 'Dueparethio'. These characteristics in combination distinguish 'Dueparethio' as a new and distinct *Artemisia* plant:

1. Relatively compact, upright and somewhat outwardly spreading growth habit.
2. Freely branching habit.
3. Moderately vigorous to vigorous growth habit.
4. Greyed green-colored leaves.
5. Good garden performance.

Plants of the new *Artemisia* can be compared to plants of the female parent selection. Plants of the new *Artemisia* differ primarily from plants of the female parent selection in plant habit as plants of the new *Artemisia* are more compact than plants of the female parent selection.

Plants of the new *Artemisia* can be compared to plants of the male parent selection. Plants of the new *Artemisia* differ primarily from plants of the male parent selection in the following characteristics:

1. Plants of the new *Artemisia* are more freely branching than plants of the male parent selection.
2. Plants of the new *Artemisia* and the male parent selection differ in leaf color as plants of the male parent selection have green-colored leaves.

Plants of the new *Artemisia* can be compared to plants of *Artemisia vulgaris* 'Oriental Limelight', disclosed in U.S. Plant Pat. No. 12,788. In side-by-side comparisons conducted in Rheinberg, Germany, plants of the new *Artemisia* differed primarily from plants of 'Oriental Limelight' in the following characteristics:

1. Plants of the new *Artemisia* were more compact than plants of 'Oriental Limelight'.
2. Plants of the new *Artemisia* were more freely branching than plants of 'Oriental Limelight'.
3. Plants of the new *Artemisia* and 'Oriental Limelight' differed in leaf color as plants of 'Oriental Limelight' had bright yellow and green variegated leaves.

BRIEF DESCRIPTION OF THE PHOTOGRAPH

The accompanying colored photograph illustrates the overall appearance of the new *Artemisia* plant showing the colors as true as it is reasonably possible to obtain in colored reproductions of this type. Colors in the photograph may differ slightly from the color values cited in the detailed botanical description which accurately describe the colors of the new *Artemisia* plant.

The photograph comprises a side perspective view of a typical plant of 'Dueparethio' grown in a container.

DETAILED BOTANICAL DESCRIPTION

The aforementioned photograph and following observations, measurements and values describe plants grown in 12-cm containers during the summer in a glass-covered greenhouse in Rheinberg, Germany and under cultural practices typically used in commercial *Artemisia* production. During the production of the plants, night temperatures averaged 18° C. and light levels averaged 4,500 lux. Plants were pinched one time about three weeks after planting and were 20 weeks old when the photograph and description were taken. In the following description, color references are made to The Royal Horticultural Society Colour Chart, 1995 Edition, except where general terms of ordinary dictionary significance are used.

Botanical classification: *Artemisia arborescens* 'Dueparethio'.

Parentage:

*Female, or seed, parent*.—Proprietary selection of *Artemisia arborescens* identified as code number A07-0231-2, not patented.

*Male, or pollen, parent*.—Proprietary selection of *Artemisia arborescens* identified as code number A07-0109-4, not patented.

Propagation:

*Type*.—By terminal cuttings.

*Time to initiate roots, summer*.—About five days at temperatures of about 20° C.

*Time to initiate roots, winter*.—About seven days at temperatures of about 20° C.

*Time to produce a rooted young plant, summer*.—About three weeks at temperatures of about 20° C.

*Time to produce a rooted young plant, winter*.—About four weeks at temperatures of about 20° C.

*Root description*.—Fine, fibrous; white in color.

*Rooting habit*.—Freely branching; dense.

Plant description:

*Plant and growth habit*.—Relatively compact, upright to outwardly spreading growth habit; freely branching habit with about ten lateral branches, dense and bushy; moderately vigorous to vigorous growth habit.

*Plant height*.—About 30 cm to 32 cm.

*Plant diameter*.—About 27.5 cm to 30 cm.

Lateral branch description:

*Length*.—About 10 cm to 40 cm.

*Diameter*.—About 4 mm to 5 mm.

*Internode length*.—About 1.25 cm to 1.5 cm.

*Strength*.—Strong.

*Aspect*.—Upright to somewhat outwardly spreading.

*Texture*.—Densely pubescent.

*Color*.—Close to 195A.

Foliage description:

*Arrangement*.—Alternate; simple.

*Length*.—About 2.5 cm.

*Width*.—About 2.8 cm.

*Shape*.—Obovate; deeply incised.

*Apex*.—Tri-dentate.

*Base*.—Acute.

*Margin*.—Deeply incised.

*Texture, upper and lower surfaces*.—Tomentose.

*Fragrance*.—Aromatic.

*Venation pattern*.—Pinnate; arcuate.

*Color*.—Developing leaves, upper and lower surfaces: Close to 191A to 191B. Fully expanded leaves, upper surface: Close to 191A; venation, close to 191A. Fully expanded leaves, lower surface: Close to 191A to 191B; venation, close to 191A to 191B.

*Petiole length*.—About 1.6 cm.

*Petiole diameter*.—About 1 mm.

*Petiole texture, upper and lower surfaces*.—Tomentose.

*Petiole color, upper and lower surfaces*.—Close to 191A to 191C.

Inflorescence description: Inflorescence initiation and development have not been observed on plants of the new *Artemisia*.

Disease/pest resistance: Plants of the new *Artemisia* have not been observed to be resistant to pathogens and pests common to *Artemisia*.

Garden performance: Plants of the new *Artemisia* have been observed to have good garden performance and tolerate temperatures ranging from about 5° C. to about 40° C.

It is claimed:

1. A new and distinct *Artemisia* plant named 'Dueparethio' as illustrated and described.

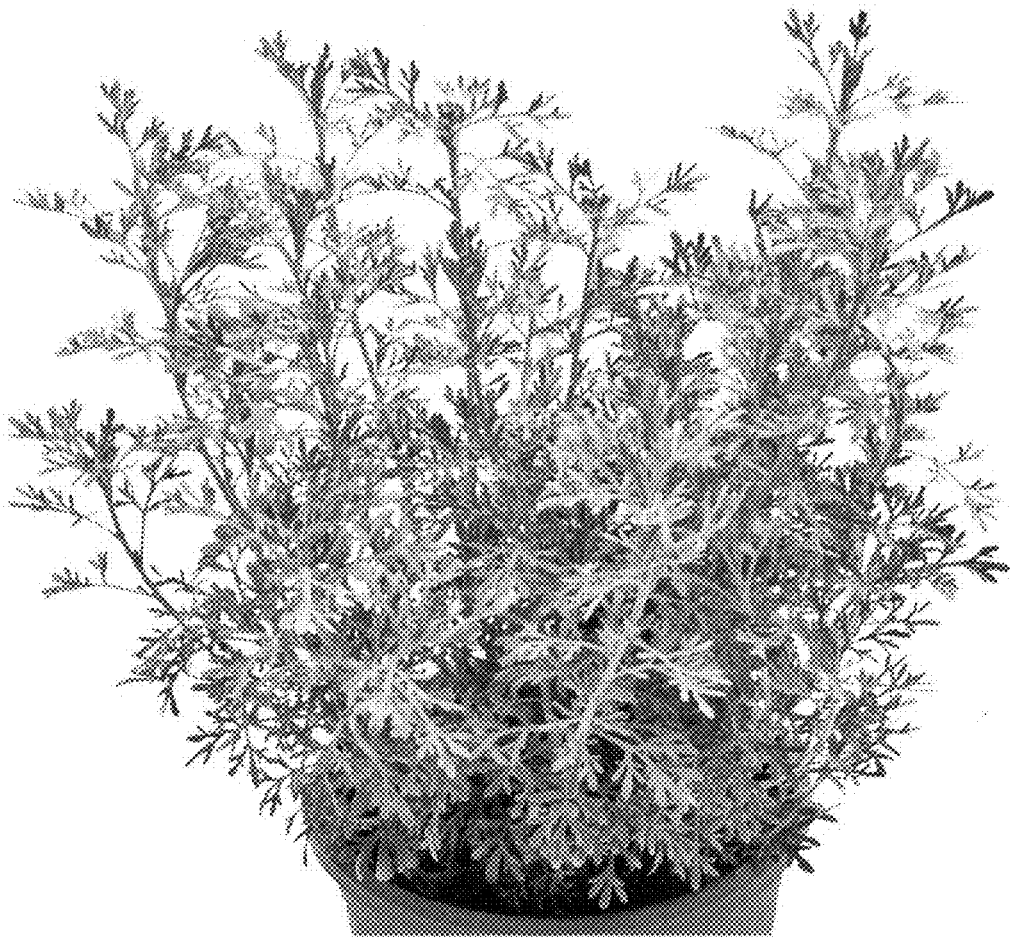

* * * * *